United States Patent [19]

Kirby et al.

[11] Patent Number: 5,415,640

[45] Date of Patent: May 16, 1995

[54] BODYSIDE COVER FOR AN ABSORBENT ARTICLE

[75] Inventors: Robert E. Kirby; Howard A. Whitehead, both of Appleton, Wis.; Mary C. Wanek; David K. Osteen, both of Marietta, Ga.; Kenneth Y. Wang, Westchester, Pa.

[73] Assignee: Kimberly-Clark Corporation, Neenah, Wis.

[21] Appl. No.: 68,806

[22] Filed: May 28, 1993

Related U.S. Application Data

[63] Continuation of Ser. No. 731,583, Jul. 17, 1991, abandoned.

[51] Int. Cl.$^6$ .............................................. A61F 13/15
[52] U.S. Cl. ..................... 604/383; 604/366; 604/381
[58] Field of Search .................. 604/378–383, 604/385.1, 366–374

[56] References Cited

U.S. PATENT DOCUMENTS

| | | | |
|---|---|---|---|
| 2,295,439 | 9/1942 | Voigtman | 128/284 |
| 2,564,689 | 8/1951 | Harwood et al. | 128/290 |
| 2,900,980 | 8/1959 | Harwood | 128/290 |
| 3,676,242 | 7/1972 | Prentice | 156/62.4 |
| 3,888,254 | 6/1975 | Hendricks | 128/290 R |
| 3,929,135 | 12/1975 | Thompson | 128/287 |
| 3,945,386 | 3/1976 | Anczurowski et al. | 128/287 |
| 3,965,906 | 6/1976 | Karami | 604/383 |
| 3,967,623 | 7/1976 | Butterworth et al. | 128/287 |
| 3,994,299 | 11/1976 | Karami | 604/383 |
| 4,014,341 | 3/1977 | Karami | 604/383 |
| 4,285,342 | 8/1981 | Mesek | 128/287 |
| 4,323,069 | 4/1982 | Ahr et al. | 128/287 |
| 4,324,246 | 4/1982 | Mullane et al. | 128/287 |
| 4,333,465 | 6/1982 | Wiegner | 128/290 R |
| 4,340,563 | 7/1982 | Appel et al. | 264/518 |
| 4,397,644 | 8/1983 | Matthews et al. | 604/378 |
| 4,480,000 | 10/1984 | Watanabe et al. | 428/284 |
| 4,519,799 | 5/1985 | Sakurai et al. | 604/366 |
| 4,578,066 | 3/1986 | O'Connor | 604/366 |
| 4,675,013 | 6/1987 | Ruffo | 604/366 |
| 4,690,679 | 9/1987 | Mattingly, III et al. | 604/383 |
| 4,710,186 | 12/1987 | DeRossett et al. | 604/383 |
| 4,725,473 | 2/1988 | Van Gompel et al. | 428/156 |
| 4,741,941 | 5/1988 | Englebert et al. | 428/71 |
| 4,755,413 | 7/1988 | Morris | 428/138 |
| 4,762,520 | 8/1988 | Wallstrom | 604/366 |
| 4,781,962 | 11/1988 | Zamarripa et al. | 428/138 |
| 4,798,603 | 1/1989 | Meyer et al. | 604/378 |
| 4,798,604 | 1/1989 | Carter | 604/383 |
| 4,806,411 | 2/1989 | Mattingly, III et al. | 428/139 |
| 4,878,974 | 11/1989 | Kagawa | 156/85 |
| 4,908,026 | 3/1990 | Sukiennik et al. | 604/378 |
| 5,019,062 | 5/1991 | Ryan et al. | 604/383 |
| 5,023,124 | 6/1991 | Kobayashi | 428/76 |

FOREIGN PATENT DOCUMENTS

| | | | |
|---|---|---|---|
| 0040084 | 11/1981 | European Pat. Off. | 604/383 |
| 0088738A1 | 3/1983 | European Pat. Off. | |
| 0272683A2 | 12/1987 | European Pat. Off. | |
| 0321985A3 | 12/1988 | European Pat. Off. | |
| 0329160A3 | 2/1989 | European Pat. Off. | |
| 0335252A3 | 3/1989 | European Pat. Off. | |
| 0347746A1 | 6/1989 | European Pat. Off. | |
| 0358031A3 | 8/1989 | European Pat. Off. | |
| 3037032 | 5/1982 | Germany | 604/383 |
| 1122727 | 2/1988 | Japan | |
| 0845826 | 8/1960 | United Kingdom | 604/383 |
| 2124908 | 2/1984 | United Kingdom | |
| WO9309744 | 5/1993 | WIPO | |

Primary Examiner—Randall L. Green
Assistant Examiner—Rob Clarke
Attorney, Agent, or Firm—Mark L. Davis

[57] ABSTRACT

A bodyside cover an for absorbent article is disclosed which includes two different materials to provide enhanced functionality. The bicomponent cover includes an apertured first material, which is positioned along the longitudinal central axis of the absorbent article, and a nonperforated second material secured to at least a portion of the first material. The first material has a rewet value which is less than, or equal to, the rewet value of the second material while the second material is softer than the first material. The first material is positioned below the principal point of fluid discharge and represents the primary fluid-receiving region of the cover. The second material is situated away from the principal point of fluid discharge and represents the secondary fluid-receiving region of the cover.

11 Claims, 5 Drawing Sheets

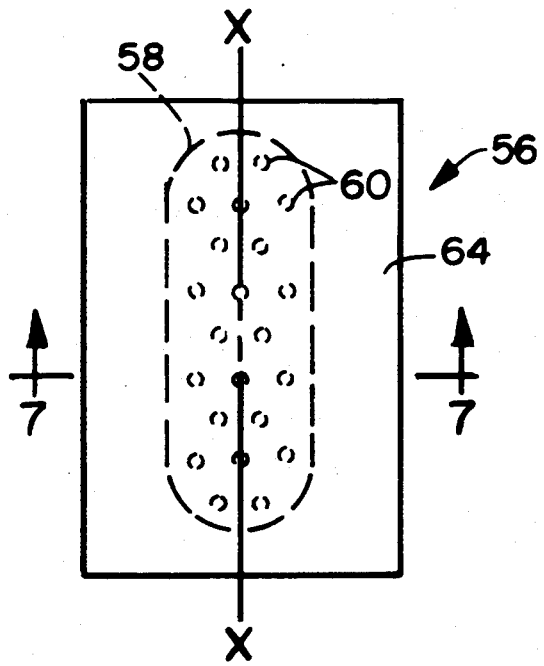
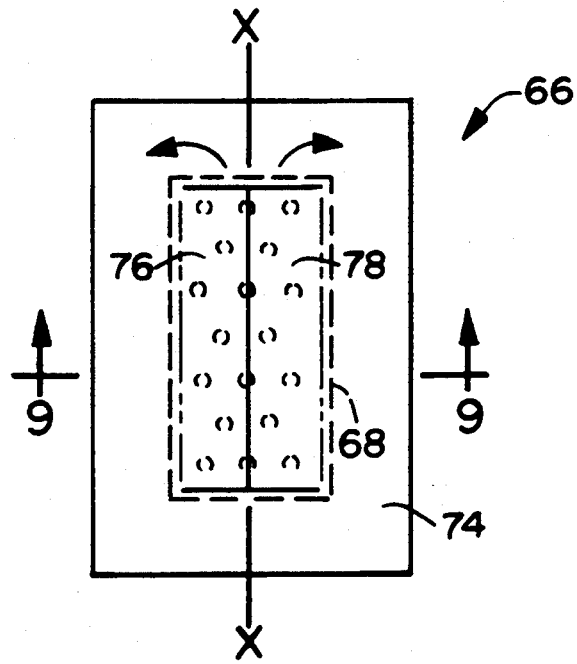
FIG. 6
FIG. 8
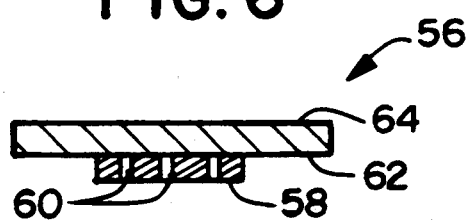
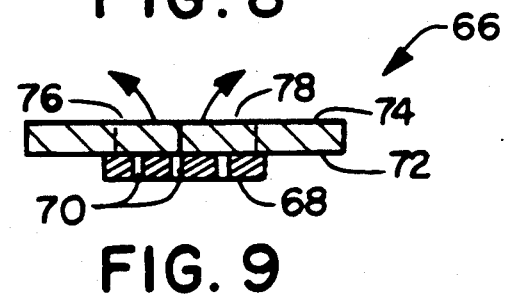
FIG. 7
FIG. 9
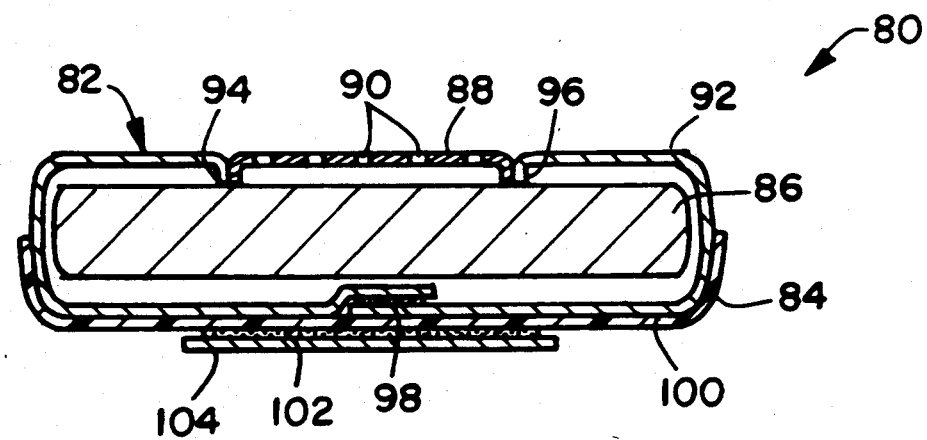
FIG. 10

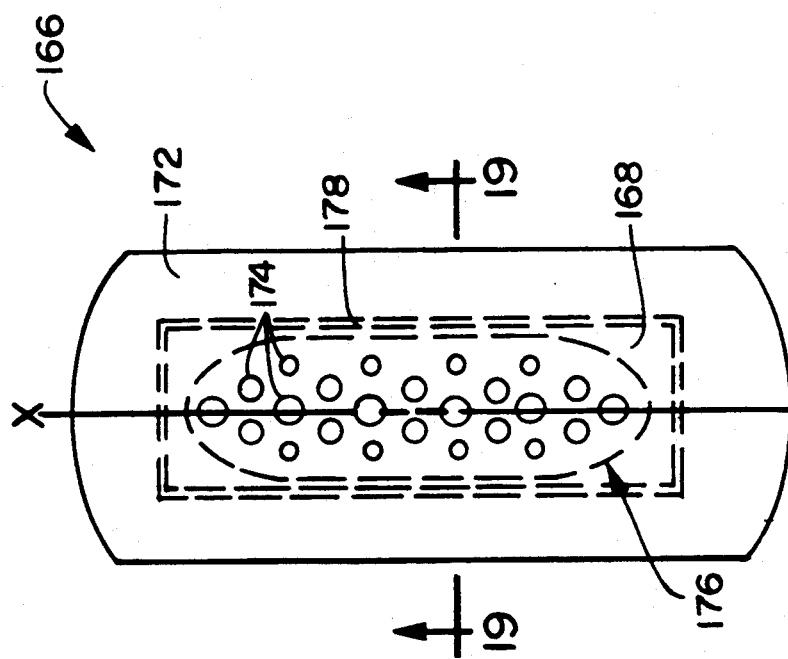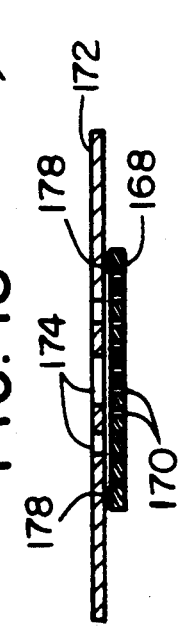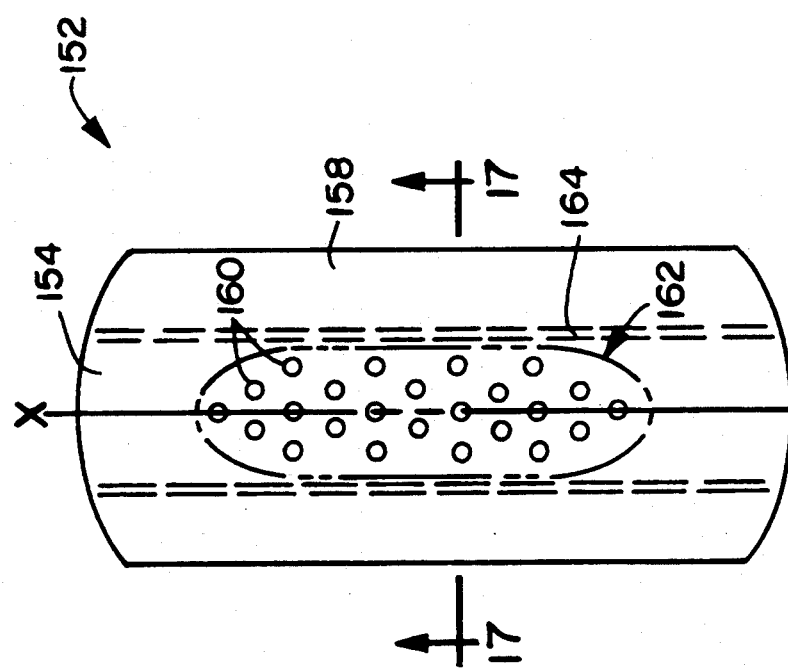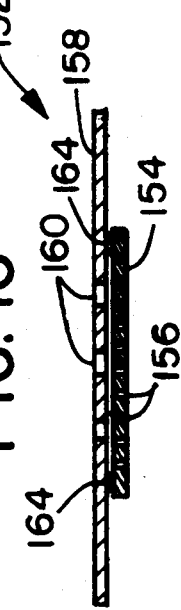

BODYSIDE COVER FOR AN ABSORBENT ARTICLE

This is a continuation application Ser. No. 07/731,583, filed on Jul. 17, 1991, now abandoned.

FIELD OF THE INVENTION

This invention relates to a bodyside cover for an absorbent article. More particularly, this invention relates to a bicomponent cover which has the properties of dryness, fluid masking and rapid fluid absorbency in a central fluid-receiving region. The bicomponent cover also provides a soft and comfortable surface adjacent to the wearer's skin.

BACKGROUND OF THE INVENTION

Disposable absorbent articles, such as sanitary napkins, catamenial pads, pantiliners, diapers, training pants, incontinent garments, and the like, are designed to be worn adjacent to a human body to absorb discharged body fluids. The body fluids can include urine, blood, menses and other excrements discharged by the body at various times, such as during a bowel movement or during a menstrual period. Such articles are normally multilayered in construction and include a liquid-permeable cover, a liquid-impermeable baffle and an absorbent positioned therebetween. The article can also include a transfer and/or distribution layer situated between the cover and the absorbent which directs body fluid downward, away from the cover and distributes the fluid in the x and y directions. The cover is designed to allow rapid transfer of body fluid down into the absorbent where it can be retained. The baffle serves to prevent fluid present in the absorbent from leaking out and soiling or staining an undergarment or another adjacent piece of clothing.

The body-contacting cover must serve many functions. First, the cover should provide a dry surface against the body of the user of the absorbent article. A measure of dryness is a low rewet value. That is, the cover should prevent rewetting of the user's skin when the absorbent article is compressed or distorted by ordinary body movement. This can be accomplished by placing a flow zone control layer beneath the cover, as taught in U.S. Pat. No. 4,908,026 issued to Sukiennik et al., or by forming uniquely shaped apertures in the cover, as taught in U.S. Pat. No. 3,929,135 issued to Thompson. Second, the cover should serve to mask the body fluid that has passed into the absorbent. This is especially true for feminine products where blood or menstrual fluid is being retained by the absorbent. Female users prefer a product having a clean appearance, and the presence of a blood stain could convey an impression that the product might leak or has to be changed immediately. Third, the cover should have sufficient openness (pore size distribution) to allow body fluid to pass quickly down into the absorbent. This can be accomplished by using a low weight material, using larger fibers with a higher denier, or by piercing or aperturing the cover. The use of a thin material, such as a tightly bonded fabric having a sufficient degree of wear resistance is also preferred. Fourth, the cover should be soft and comfortable against the user's skin. Portions of the user's torso, crotch, legs, thighs and buttocks may come in direct contact with at least a portion of the absorbent article. Fifth, the cover should be easy to manufacture, and lastly it should be relatively inexpensive.

Numerous prior art patents exist which teach different materials and constructions for the cover layer. The initial use of nonwoven materials has evolved into the use of one or more nonwoven fibrous layers, along with a film layer containing apertures. U.S. Pat. Nos. 3,945,386; 3,965,906; 3,967,623; 3,994,299; 4,014,341; 4,323,069 and 4,324,246 teach such combinations. Other patents, such as U.S. Pat. Nos. 3,888,254 and 4,675,013, teach the use of a cover layer which is laminated to other fibrous sheets. U.S. Pat. No. 4,762,520 teaches forming a cover from a carded fiber fabric containing melt fibers sub-divided into parallel streaks. Other U.S. patents, such as U.S. Pat. Nos. 4,710,186; 4,755,413; 4,798,604 and 4,806,411, teach forming apertures in the cover. U.S. Pat. No. 4,333,465 teaches a cover comprised of a liquid-impermeable composite material having a liquid-permeable zone. Lastly, U.S. Pat. Nos. 3,676,242; 4,690,679; 4,725,473 and 4,878,974 teach various methods of making film and fiber composite cover materials by coextrusion, laminating, etc.

Two patent applications filed by Kimberly-Clark Corporation, which relate to nonwoven webs, include U.S. Ser. No. 07/608,095, filed Nov. 1, 1990, by inventors H. K. Barnes et al., entitled "HYDRAULICALLY NEEDLED NONWOVEN PULP FIBER WEB and "U.S. Ser. No. 07/633,594, filed Dec. 21, 1990, by inventors C. Everhart et al., entitled "HIGH PULP CONTENT NONWOVEN COMPOSITE FABRIC."

Presently, some manufacturers are moving toward the use of two or more different kinds of materials for the cover in order to enhance the functionality of the cover layer. Published Japanese patent application 122,727 (1989) teaches a sanitary napkin which has a cover constructed of two different hydrophobic materials, both of which contain apertures. U.S. Pat. No. 4,285,342 issued to Mesek is somewhat similar except, instead of using two different kinds of materials, a large opening is formed in the cover layer of a diaper to enhance fluid flow into the absorbent. U.K. patent 2,124,907 issued to Lloyd teaches a fabric bonded to a water-impermeable material, with both materials located on the bodyside surface of the absorbent device.

In order for an absorbent article to exhibit improved fluid management, it should utilize one or more layers located between the cover and the absorbent. Such layer(s) should assist in keeping the cover dry by directing body fluid downward, away from the cover. The layers can also function to move the body fluid outward, in the x and y directions, so as to facilitate rapid fluid intake by the absorbent. U.S. patents, which teach the use of a fluid transfer or a fluid distribution layer beneath the cover, include U.S. Pat. Nos. 4,397,644; 4,480,000; 4,519,799 and 4,798,603. These patents teach various materials and compositions for the transfer or distribution layer which assist in directing the body fluid downward, into the absorbent.

Most of the cover materials described in the above-identified patents do not function as effectively as most consumers would prefer. Some covers exhibit a rapid fluid flow-through rate but have a harsh or irritating surface against the user's skin. Covers made from spunbond or carded webs are soft and comfortable but offer little in the way of dryness or fluid masking. Furthermore, some covers are difficult to manufacture and/or are expensive. Because of this, there is a need for a cover which is relatively inexpensive, easy to manufacture and which functions better than current, commercially available materials.

Now a bodyside cover has been invented which provides softness and comfort adjacent to a user's skin while having the properties of dryness, good fluid masking and rapid fluid transfer.

SUMMARY OF THE INVENTION

Briefly, this invention relates to a bodyside cover for an absorbent article which includes two different kinds of materials to provide enhanced functionality. The bicomponent cover includes a first material and a second material. The first material, which can be an extrusion-coated nonwoven web, a thermoplastic film or a net has a plurality of apertures formed therethrough and is positioned along the longitudinal central axis of the absorbent article. The second material, which is preferably a nonwoven web, is nonperforated and is aligned adjacent to and secured to at least a portion of the outer periphery of the first material. The first material, when incorporated into a product, has an absorbency rate which is about equal to, or greater than, the absorbency rate of the second material. The first material is positioned below the principal point of discharge of the body fluid and serves as the primary fluid-receiving region of the bicomponent cover. The second material is situated away from the principal point of discharge of the body fluid and forms the secondary fluid-receiving region of the bicomponent cover.

The general object of this invention is to provide a bodyside cover for an absorbent article. A more specific object of this invention is to provide a bicomponent cover for an absorbent article which provides softness and comfort to the user's skin while having improved functionality in that it exhibits dryness, good fluid masking and rapid fluid transfer.

Another object of this invention is to provide a bodyside cover for an absorbent article which is relatively inexpensive.

A further object of this invention is to provide a bicomponent cover having primary and secondary fluid-receiving regions.

Still further, an object of this invention is to provide an absorbent article having a bicomponent cover comprised of an apertured film which is at least partially surrounded by a nonperforated nonwoven web.

Other objects and advantages of the present invention will become more apparent to those skilled in the art in view of the following description and the accompanying drawings.

BRIEF DESCRIPTION OF THE DRAWINGS

FIG. 6 is a top view of still another embodiment of a bicomponent cover showing a racetrack-shaped, apertured first material positioned below a second material.

FIG. 7 is an end view of the bicomponent cover shown in FIG. 6 depicting placement of the first material below the second material.

FIG. 8 is a top view of another embodiment of a bicomponent cover showing an apertured first material positioned below a second material which has a pair of flaps formed therein.

FIG. 9 is an end view of the bicomponent cover shown in FIG. 8 depicting placement of the first material below the second material.

FIG. 10 is a cross-sectional view of an absorbent article having a bicomponent cover, an absorbent enclosed by the bicomponent cover and a liquid-impermeable baffle positioned external of the cover and adjacent to the garment-facing surface of the absorbent.

FIG. 16 is a top view of another embodiment of a bicomponent cover showing an apertured first material positioned below an apertured second material.

FIG. 17 is a cross-sectional view of the bicomponent cover shown in FIG. 16 taken along line 17—17 depicting the apertured first material secured to a portion of the lower surface of the apertured second material.

FIG. 18 is a top view of another embodiment of a bicomponent cover showing an apertured first material positioned below an apertured second material and having different sized apertures formed therethrough.

FIG. 19 is a cross-sectional view of the bicomponent cover shown in FIG. 18 taken along line 19—19 depicting the apertured first material bonded to a portion of the lower surface of the apertured second material.

DETAILED DESCRIPTION OF THE PREFERRED EMBODIMENTS

Figure 1:
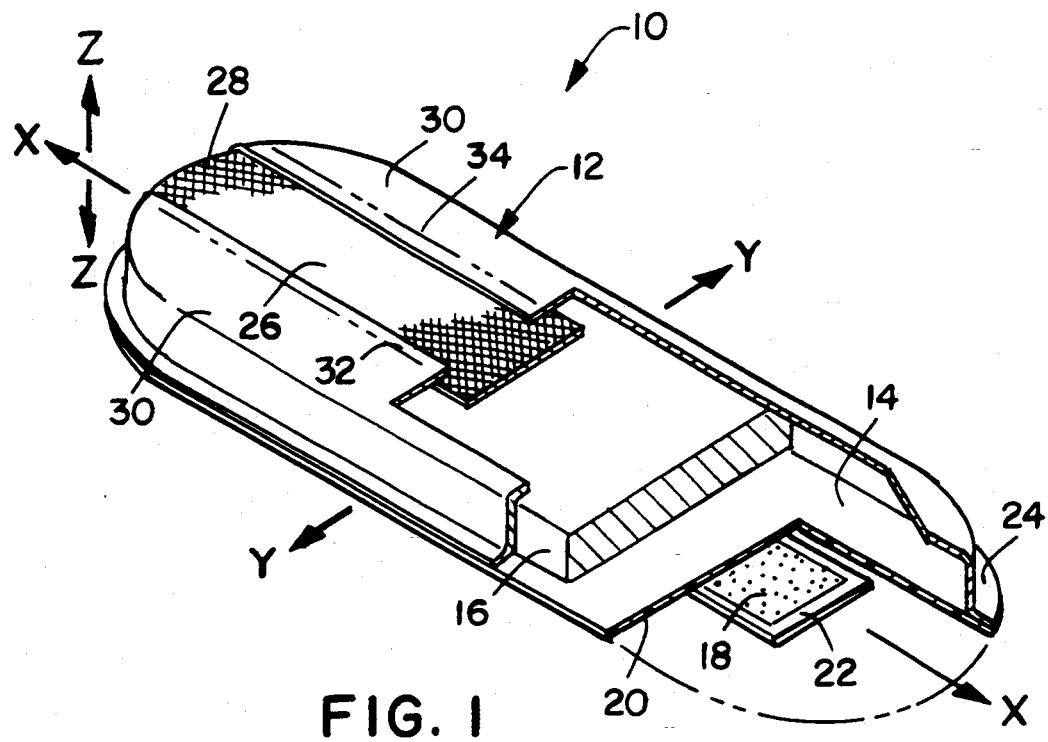
FIG. 1 is a perspective view, partially sectioned, showing an absorbent article, in the form of a sanitary napkin, having a bicomponent cover constructed of an apertured first material partially overlapped by a second material.

Referring to FIG. 1, an absorbent article 10, in the form of a sanitary napkin, is shown having a multi-layered construction. The absorbent article 10 includes a liquid-permeable bicomponent cover 12, a liquid-impermeable baffle 14 and an absorbent 16 positioned therebetween. The bicomponent cover 12 cooperates with the baffle 14 to completely enclose the absorbent 16. The bicomponent cover 12 is designed to be positioned against the body of the user, while the baffle 14 is positioned adjacent to an undergarment. Although the absorbent article 10 is depicted as a sanitary napkin, it could be a catamenial pad, a pantiliner, a diaper, training pants, incontinent garment, or the like.

The absorbent article 10 is an elongated member having a longer length than width. The length extends along the x axis, the width extends along the y axis, and the thickness extends along the z axis. A garment adhesive strip 18 is secured to an exterior surface 20 of the baffle 14. It should be noted that two or more adhesive strips could be used in place of the single adhesive strip 18, if desired. A removable peel strip 22 is positioned over the adhesive strip 18 and is designed to be removed by the user before the sanitary napkin is attached to the interior surface of an undergarment.

The absorbent article 10 also contains a peripheral seal 24 which is formed by securing the bicomponent cover 12 to the baffle 14. This seal 24 assures that the absorbent 16 is completely enclosed.

The bicomponent cover 12 is constructed of two different and distinct materials 26 and 30. The first material 26 preferably contains a plurality of apertures 28 formed therethrough, while the second material 30 is preferably nonapertured. The first material 26 can be a thermoplastic film, an extrusion-coated nonwoven, or a net material that has openings between the strands or threads due because of it's construction. Useful thermoplastic films include polyolefin materials, such as polyethylene, which can be manufactured in various forms. Such films and film making processes are commercially available from the following companies:

Smith & Nephew Plastic, Ltd. Gilberdyke, Brough North Humderside HU15 2TD United Kingdom Applied Extrusion Technologies, Inc. P.O. Box 582 Middleton, Del. 19709

Fameccanica Fraz Sambuceto I-66020 San Giovanni Teatino Italy

LCL Manufacturing PTE Ltd. 16 Pandan Rd. Singapore 2260

The first material 26 can also be a net, an embossed net, an extruded netting or a net formed from strands of filaments or threads. Examples of covers constructed of netting are taught in U.S. Pat. Nos. 2,295,439; 2,564,689; 2,900,980 and 4,741,941. These patents are incorporated by reference and made a part hereof. The open spaces between the filaments or threads of the netting serve the same function as the apertures or perforations formed through a thermoplastic film. The first material 26 can also be a foam material having a plurality of apertures formed therethrough.

An extrusion-coated nonwoven includes a laminate film composite and normally refers to a class of composite materials wherein a lower substrate ply is either mechanically, thermally or chemically adhered to an upper film based ply. The substrate may consist of any nonwoven including bonded carded webs, spunbond webs, meltblown webs or cellulose-based tissues. The upper film ply can be an apertured plastic film, a cast continuous film which would be apertured prior to application to the substrate or be a net material.

The first material 26 has a thickness of less than about 2 millimeters and preferably between about 0.05-2.0 millimeters. The first material 26 can have a three-dimensional (3-D) profile to give it extra thickness and enhance its functionality. One way to acquire a 3-D profile is to emboss the material between the nip of a pair of rollers.

The apertures 28 formed in the first material 26 can vary in size, shape and pattern. The apertures 28 can be arranged in either a systematic, uniform or random pattern. A systematic pattern, with similarly sized apertures, is preferred. The apertures 28 can constitute about 20–70 percent, preferably about 30–60 percent, and most preferably about 30–50 percent of the total exposed surface area of the first material 26. "Total exposed surface area" is defined as that area of the bicomponent cover 12 which faces the body of the user. The apertures 28 can be formed by mechanically perforating the material, such as by needling or punching, be formed by hot vacuum drawing, or be formed by other methods known to those skilled in the art. The apertures 28 should be formed through the entire thickness of the first material 26. It should be noted that the geometrical shape of the sidewalls of each aperture 28 can vary. For example, the apertures 28 can be round, triangular, square, or irregular in cross-sectional shape. The sidewalls of the apertures 28 can be aligned perpendicularly to the top plane of the first material 26 or they can be slanted at a desired angle.

When forming the apertures 28 in the first material 26, it is possible to form the apertures 28 such that the apex of each extends below the base plane of the first material 26. This configuration will allow the sidewalls of each aperture 28 to contact and penetrate the fibers of an adjacent layer, for example, a cellulose pulp layer or a separation layer. This can be advantageous in providing rapid transfer of body fluid down, into the absorbent or into a separation layer.

The first material 26 is positioned about the longitudinal central axis x—x of the absorbent article 10 and constitutes the primary fluid-receiving region of the bicomponent cover 12. The absorbent article 10 is positioned adjacent to the human body such that the principal point of discharge of body fluid or excrement, whether it be from the urethra, the vaginal orifice, or the anus, is in direct alignment with the upper surface of the first material 26. The first material 26 can be of varying lengths and widths and can have various shapes. For a sanitary napkin, a rectangular, oval or racetrack-shaped configuration is preferred, and the length should be greater than about 2 inches (50.8 mm), preferably greater than about 3 inches (76.2 mm), and most preferably greater than at least half of the length of the entire absorbent article 10. The first material 26 can also have a length equal to the length of the absorbent article 10, as is shown in FIG. 1. For ease in manufacture, it may be advantageous to make the length of the first material 26 equal to, slightly less than, the overall length of the absorbent article 10. A length of at least 50% of the length of the absorbent article 10 is sufficient for most applications. For diapers, training pants or incontinent garments, where more material is utilized, it is beneficial to limit the length of the first material 26 to between about 2–10 inches (50–254 mm).

The first material 26 can have varying widths. For a sanitary napkin, a width of between about 0.25–3.0 inches (6.4–76.2 mm) is sufficient. A preferred width is between about 0.75–2.5 inches (19–63.5 mm), and a most preferred width is about 1.0–2.0 inches (25.4–50.8 mm). Generally, for feminine products, a width of about 25–95%, and preferably about 40–60% of the width of the absorbent article is acceptable. For diapers, training pants and incontinent garments, a width of less than 5.0 inches (127 mm) is sufficient.

In FIG. 1, the first material 26 is shown forming a smaller portion of the exposed surface area of the bicomponent cover 12 than the second material 30. The reason for this is that, when the first material 26 is a thermoplastic film and the second material 30 is a nonwoven web, the film is more expensive than the nonwoven web, and therefore it is beneficial to use less of it. Even though the second material 30 occupies a larger portion of the exposed surface area of the bicomponent cover 12 than the first material 26, it is possible to have the first material 26 form an equal or larger portion of the bicomponent cover 12, if desired.

The second material 30 of the bicomponent cover 12 is preferably a liquid-permeable nonwoven web. The nonwoven web can be a fibrous material formed from fusible polymeric fibers or filaments. The nonwoven web is nonperforated, although a perforated web can be used if desired. The nonwoven web can be formed from any of the following polymers: polyamides, polyesters, polyolefins, polyvinyl acetate, polyvinyl chloride, polyvinyl alcohol, cellulose acetate, viscose, and the like. Suitable materials include polypropylene spunbond and bonded carded webs. An appropriate nonwoven web material should have a uniform web with a denier of about 1.5 or greater. Such a material, commonly referred to as a linear drawn spunbond, is described in U.S. Pat. No. 4,340,563 issued to Appel et al. and is hereby incorporated by reference and made a part hereof.

In FIG. 1, the second material 30 overlaps a portion of the longitudinal side edges of the first material 26 and is bonded along lines 32 and 34. The second material 30 can be bonded to the first material 26 by a mechanical attachment, an adhesive, an ultrasonic bond, a thermal bond, a pressure bond or a combination of both heat and pressure. Other means of attaching the two materials together can also be used. It should be noted that the first material 26 can be bonded to the second material 30 before the apertures 28 are formed therethrough, or vice versa. The bicomponent cover 12 can be constructed off-line and then assembled into an absorbent article 10, or it can be constructed on-line.

The second material 30 is secured to the first material 26 and forms a secondary fluid-receiving region of the bicomponent cover 12. The second material 30 is spaced away from the principal point of discharge of body fluid which the absorbent article 10 is designed to receive. It should be noted that, even though the second material 30 is designated as the secondary fluid-receiving region of the bicomponent cover 12, it still has the ability to allow fluid to pass down through it and into the absorbent 16. The absorbency rate of the second material 30, which is defined as the amount of time it takes for a material to absorb a certain quantity of fluid, is about equal to or less than the absorbency rate through the first material 26. Accordingly, most of the body fluid, under normal conditions, is designed to pass down into the absorbent 16, through the first material 26.

Rewet values represent a measure of the surface dryness of a material. A lower value indicates a material which exhibits a drier surface. Rewet values for the bicomponent cover 12 were obtained and are listed in Tables 1, 2 and 3 below. The actual rewet test involved infusing a product with 8 cubic centimeters (cc) of distilled water and measuring the amount of distilled water, in grams, which exited the product under 1 psi pressure.

TABLE 1

REWET VALUES
FIRST MATERIAL WITH SEPARATION MEANS

| | | REWET (gm) |
|---|---|---|
| Material 1 | Extrusion-Coated Nonwoven (ECNW) 0.75 mil polypropylene (PP) film/0.8 ounces per square yard (osy) PP spunbond 1.5 osy PP spunbond-separation means | 0.08 |
| Material 2 | Two dimensional netting 1.5 osy PP spunbond-separation means | 0.07 |
| Material 3 | Three dimensional apertured film 1.5 osy PP spunbond-separation means | 0.08 |

TABLE 2

FIRST MATERIAL WITHOUT SEPARATION MEANS

| | | REWET (gm) |
|---|---|---|
| Material 1 | Extrusion-Coated Nonwoven (ECNW) 0.75 mil PP film/0.8 osy PP spunbond | 0.04 |
| Material 2 | Two dimensional netting 24 grams per square meter, 0.07 m bulk | 2.11 |
| Material 3 | Three dimensional apertured film 35 grams per square meter, 0.65 mm bulk | 0.60 |

TABLE 3

SECOND MATERIAL WITHOUT SEPARATION MEANS

| | | REWET (gm) |
|---|---|---|
| Material 1 | SPUNBOND 0.4 osy polypropylene spunbond (5 denier) | 1.92 |
| Material 2 | SPUNBOND 0.6 osy 97% polypropylene/3% polyethylene spunbond (5 denier) | 1.52 |
| Material 3 | BONDED CARDED WEB 48 grams per square meter polypropylene, 75% hydrophobic, 25% hydrophilic, thermally bonded | 0.40 |
| Material 4 | THERMAL BONDED CARDED WEB 22 grams per square meter polypropylene, thermally bonded | 1.63 |

The rewet data shows that the rewet values for the first material ranged from 0.04 to 2.11 grams, and the rewet values for the second material ranged from 0.4 to 1.92 grams. Without the presence of a separation layer, it is preferred that the first material be either an apertured thermoplastic film or an extrusion-coated nonwoven material, since both exhibit low rewet values. The addition of a separation layer expands the range of candidates for the first material due to the synergistic effect of lowering the rewet value that occurs when combining the first material with a separation layer.

The bicomponent cover 12 should contain a first material that has a rewet value of less than about 2.5 grams and preferably less than about 1.5 grams. The second material should have a rewet value of less than about 3.0 grams. In addition, the rewet value of the first material 26 should be equal to or less than the rewet value of the second material 30. It should be noted that the bicomponent cover 12 is not limited only to those materials listed in the Tables but can include other materials as well. The materials listed in the Tables were selected to show the potential ranges of the data.

Absorbency rate is a measure of the time required for a product to absorb 8 cubic centimeters (cc) of fluid which has been deposited onto a cover material. Therefore, a shorter period of time indicates that the cover material will allow the fluid to pass through more quickly. The bicomponent cover 12 was tested for absorbency, and the results are listed in Table 4. The fluid used to test the various materials in Table 4 was Z-date. Z-date is a synthetic menstrual fluid that can be obtained from Kimberly-Clark Corporation, 401 N. Lake Street, Neenah, Wis., 54956.

TABLE 4
ABSORBENT RATE DATA

| | | RATE (sec) |
|---|---|---|
| FIRST MATERIAL | | |
| Material 1 | Extrusion-Coated Nonwoven (ECNW) 0.75 mil polypropylene film/0.8 ounces per square yard (osy) polypropylene spunbond | 5.66 |
| Material 2 | Three dimensional apertured film 0.49 mm bulk, 35 grams per square meter | 13.3 |
| Material 3 | Two dimensional netting | 7.54 |
| Material 4 | DRI-WEAVE Three dimensional apertured film | 10.63 |
| SECOND MATERIAL | | |
| Material 5 | SPUNBOND 100% polypropylene, 0.4 osy, 5 denier | 13.63 |
| Material 6 | SPUNBOND 97% polypropylene/3% polyethylene, 0.6 osy, 5 denier | 12.04 |
| Material 7 | SPUNBOND 97% polypropylene/3% polyethylene, 0.8 osy, 3 denier | 15.13 |

Table 4 lists absorbency rate ranges for both the first and second materials. The measured absorbency rates for the first material ranged from 5.6 to 13.3 seconds, while the measured absorbency rates for the second material ranged from 12.04 to 15.5 seconds. It should be noted that, preferably, the first material will have a faster absorbency rate than the second material, that is, the measured value will be a lower number.

The bicomponent cover 12 should have a first material with an absorbency rate of about 20 seconds or less, while the second material should have an absorbency rate of about 25 seconds or less.

A softness comparison was made between the first and second materials, 26 and 30 respectively, of the bicomponent cover 12, and the results are listed in table 5. In the test, the first material 26 was an apertured thermoplastic film, and the second material 30 was a copolymer spunbond. The Kawabata softness system was employed which utilizes four pieces of equipment. The equipment included a KES-FB1 tensile, shear tester; a KES-FB2 pure bending tester; a KES-FB3 compression tester; and a KES-FB4 friction, roughness tester. All of the equipment is commercially available from Kato Tech Co., Ltd. 26 Karato-Cho, Nishikujo Minami-Ku, Kyoto 601 Japan. Six parameters of softness were measured and they included: bending, surface friction, surface roughness, shear, compression and tensile strength.

TABLE 5
KAWABATA SOFTNESS DATA

| PARAMETER* | TEST* | FIRST MATERIAL# | SECOND MATERIAL^ |
|---|---|---|---|
| BENDING | BENDING RIGIDITY (gfXcm2/cm) | 0.028 | 0.002 |
| SURFACE FRICTION | COEFFICIENT OF FRICTION | 0.253 | 0.200 |
| SURFACE ROUGHNESS | GEOMETRICAL ROUGHNESS (micron) | 5.411 | 4.115 |
| SHEAR | SHEAR RIGIDITY (gf/cmXdegree) | 2.32 | 0.48 |
| COMPRESSION | THICKNESS LOSS DURING COMPRESSION (%) | 13.17 | 45.77 |
| TENSILE | TENSILE ENERGY (gfXcm/cm2) | 1.12 | 0.40 |

*All measurements were made in the machine direction (MD)
First material was a 35 grams per square meter, three dimensional embossed apertured film, 0.65 mm bulk
^Second material was a 0.6 ounce per square yard, copolymer spunbond The data indicates that significant differences in softness existed between the first and second materials. For all of the tests except the test for the second material, "Thickness Loss During Compression," a lower value was obtained indicating a softer material. For example, in the test for "Bending Rigidity," the 0.002 value for the second material is much lower than the 0.028 value obtained for the first material. This means that the second material (the nonwoven) is less rigid than the first material (the thermoplastic film). For the "Thickness Loss During Compression" test, a higher value indicates a more compressible and, thereby, softer material. In Table 5, the 45.77 value for the second material is higher than the 13.17 value obtained for the first material, and therefore the second material is more compressible.

The bicomponent cover 12 preferably contains a second material 30 which is softer than the first material 26 in at least one, preferably in at least three, more preferably in at least five, and most preferably in all of the six parameters using the Kawabata Evaluation System.

Figure 2:
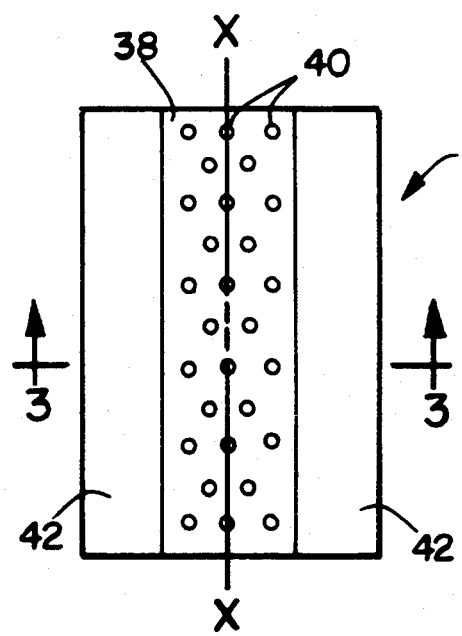
FIG. 2 is a top view of another embodiment of a bicomponent cover showing a single layer comprised of an apertured first material flanked by a second material.
Figure 3:
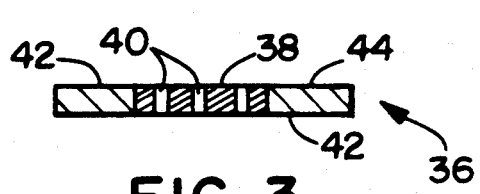
FIG. 3 is an end view of the bicomponent cover shown in FIG. 2 depicting the single layer aspect of the bicomponent cover.

Referring to FIGS. 2–3, an embodiment is shown for attaching a first material to a second material. A bicomponent cover 36 is shown having an elongated first material 38 with a plurality of apertures 40 formed therethrough. The apertures 40 have a similar size and are systematically arranged. The first material 38 is flanked and bonded to a second material 42, preferably a nonwoven web, to form a single layer having a uniform thickness. The top surface 44 of the bicomponent cover 36 is relatively smooth and does not contain any dimples or indentations.

Figure 4:
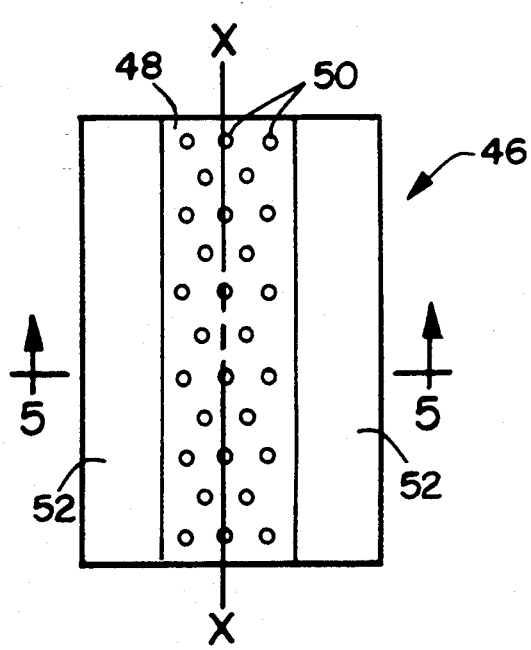
FIG. 4 is a top view of another embodiment of a bicomponent cover showing an apertured first material secured to the upper surface of a second material.
Figure 5:
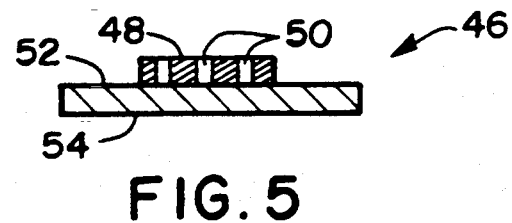
FIG. 5 is an end view of the bicomponent cover shown in FIG. 4 depicting placement of the apertured first material on top of the second material.

In FIGS. 4 and 5, a bicomponent cover 46 is shown having a first material 48 with a plurality of apertures 50 formed therethrough. The apertures 50 have a similar size and are randomly arranged. The first material 48 is secured to an upper surface 52 of a second material 54, preferably a nonwoven web. In this embodiment, the bicomponent cover 46 most likely is thicker than the single layer depicted in FIG. 3.

In FIGS. 6 and 7, a bicomponent cover 56 is shown having a first material 58 with a plurality of apertures 60 formed therethrough. The apertures 60 are randomly arranged. The first material 58 is secured to a lower surface 62 of a second material 64, preferably a nonwoven web. In this embodiment, the length of the first material 58 is less than the overall length of the bicomponent cover 56. Furthermore, the first material 58 has a racetrack-shaped configuration forming a window in the bicomponent cover 56.

In FIGS. 8 and 9, a bicomponent cover 66 is shown having a first material 68 with a plurality of apertures 70 formed therethrough. The first material 68 is secured to a lower surface 72 of a second material 74, preferably a nonwoven web. The second material 74 is slit and has a pair of parallel flaps 76 and 78 positioned vertically, above the first material 68. The flaps 76 and 78 are designed to be folded back, before the bicomponent cover 66 is brought into contact with the user's perineum. This will assure that any discharge of body fluid will directly impinge on the first material 68. In this embodiment, the first material 68 is rectangular and has a length which is less than the overall length of the bicomponent cover 66.

Referring to FIG. 10, an absorbent article 80 is shown having a liquid-permeable bodyside cover 82, a liquid-impermeable baffle 84 and an absorbent 86. The liquid-impermeable baffle 84 can be made from a microembossed polymeric film, such as polyethylene or polypropylene, or it can be made from bicomponent films. A preferred material is polyethylene. The absorbent 86 can be made from natural or synthetic fibers including cellulose fibers, surfactant-treated meltblown fibers, wood pulp fibers, regenerated cellulose or cotton fibers, or coform, which is a blend of pulp and synthetic meltblown fibers. Preferred materials can include wood pulp fluff or coform, depending upon the particular absorbent article. A hydrocolloidal material, commonly referred to as a superabsorbent, can be added to the absorbent fibers to increase absorbency and retention of body fluid. Likewise, a laminate structure containing a superabsorbent material can be used as the absorbent.

The bicomponent cover 82 is formed by combining two distinct materials. A first material 88, such as a net material, a thermoplastic film, or an extrusion-coated nonwoven which has a plurality of apertures 90 formed therethrough, is positioned along the longitudinal central axis of the absorbent article 80. The first material 88 is bonded to a second material 92, preferably a nonwoven web, at its side edges 94 and 96. In this embodiment, the bicomponent cover 82 is wrapped completely around the absorbent 86 and is secured on the garment-facing side of the absorbent article 80 by a construction adhesive 98. The liquid-impermeable baffle 84 is positioned over the exterior of the bicomponent cover 82 and is secured by additional construction adhesive 100. A garment adhesive strip 102 is secured to the external surface of the baffle 84 and is protected by a removable peel strip 104.

Figure 11:
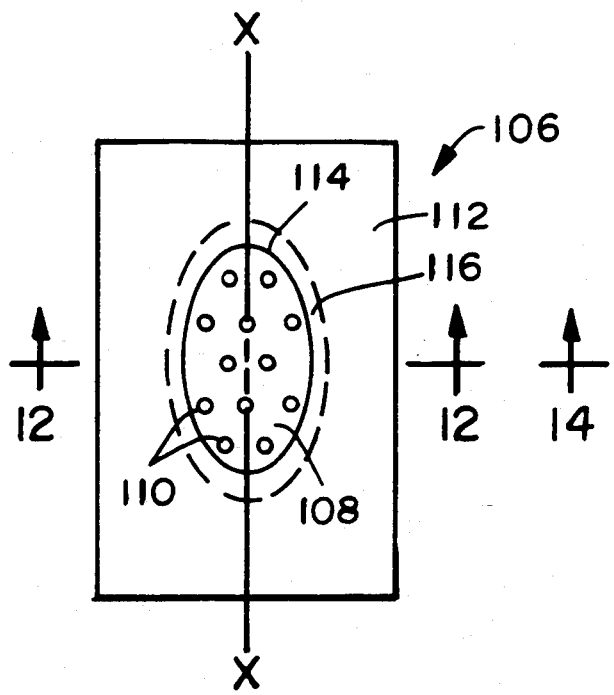
FIG. 11 is a top view of a another embodiment of a bicomponent cover showing an oval-shaped, apertured first material secured to and surrounded by a second material.
Figure 12:
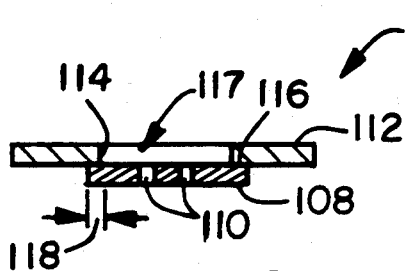
FIG. 12 is a cross-sectional view of the bicomponent cover shown in FIG. 11 taken along line 12—12 depicting the apertured first material secured to a portion of the lower surface of the second material.

Referring to FIGS. 11 and 12, an alternative embodiment is shown for bonding the first material to the second material and also for shaping the profile of the first material. A bicomponent cover 106 is depicted having an oval-shaped first material 106 with a plurality of apertures 108 formed therethrough. The actual shape of the first material 106 can be changed to suit one's particular needs. Shapes such as a rectangle, a square, a circle, or an irregular geometrical shape can be employed. A second material 112, preferably a nonwoven web, with an enlarged opening 114 formed therein, is positioned over the first material 106, and the outer periphery of the first material 106 is bonded at seal line 116 to the second material 112. This construction produces a single layer bicomponent cover 106 having a stepped configuration 117 and a small overlap portion 118. The oval-shaped first material 106 is designed to be positioned directly below the orifice in the human body from which fluid will be discharged.

Figure 13:
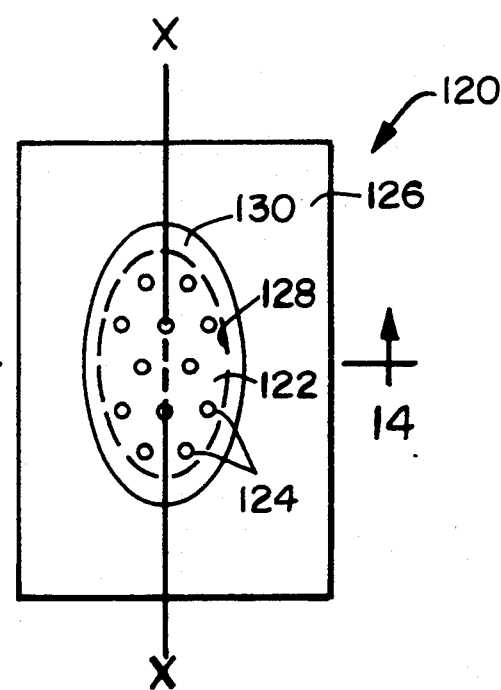
FIG. 13 is a top view of another embodiment of a bicomponent cover showing an oval-shaped, apertured first material secured to and surrounded by a second material.
Figure 14:
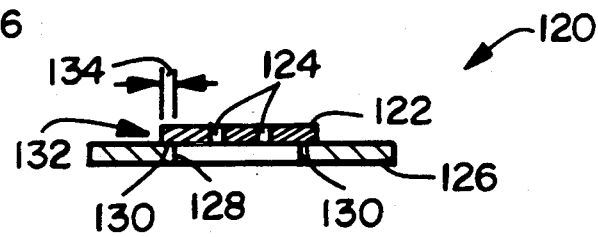
FIG. 14 is a cross-sectional view of the bicomponent cover shown in FIG. 13 taken along line 14—14 depicting the apertured first material secured to a portion of the upper surface of the second material.

Referring to FIGS. 13 and 14, another embodiment is shown wherein a bicomponent cover 120 is depicted having an oval-shaped first material 122 with a plurality of apertures 124 formed therethrough. A second material 126, preferably a nonwoven web having an enlarged opening 128 formed therein, is positioned beneath the first material 122. The outer periphery of the first material 122 is bonded at 130 to the second material 126. This construction produces a single layer bicomponent cover 120 having a stepped configuration 132 which exhibits a small overlapped portion 134. It should be noted that the entire outer periphery of the first material 122 should be bonded to the second material 126. However, only a portion of the outer periphery could be secured, if desired. Since the thickness of the first material 122 is very thin, the finished bicomponent cover 120 will exhibit a relatively smooth top surface.

Figure 15:
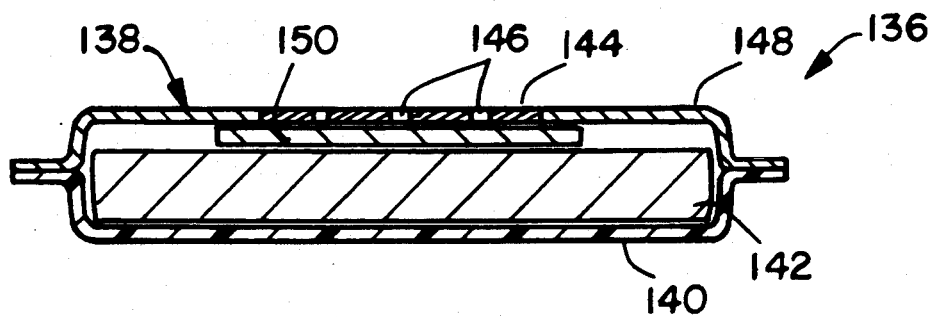
FIG. 15 is a cross-sectional view of another absorbent article having a bicomponent cover and a liquid-impermeable baffle enclosing a separation layer and an absorbent.

Referring to FIG. 15, still another alternative absorbent article 136 is shown having a multi-layered construction. The article 136 contains a liquid-permeable bicomponent cover 138, a liquid-impermeable baffle 140 and an absorbent 142 positioned therebetween. The bicomponent cover 138 is formed of a first material 144, such as a thermoplastic film or an extrusion-coated nonwoven, which has a plurality of apertures 146 formed therethrough. The first material 144 is integrally bonded to a second material 148, preferably a nonwoven web, so as to form a smooth top surface. The first material 144 and the second material 148 are shown as having an equal and uniform thickness, although it is possible to make one of the materials thinner, if desired. A separation layer 150 is situated between the bicomponent cover 138 and the absorbent 142. The separation layer 150 functions in conjunction with the bicomponent cover 138 to provide a dry surface adjacent to the user's skin.

The separation layer 150 can be constructed of a material like spunbond, meltblown, coform, tissue, hydroentangled fluff, or be a bonded carded web. The separation layer 150 functions to transfer body fluid deposited onto the bicomponent cover 138 downward, in the z direction, into the absorbent 142 and can also distribute the fluid in the x and y directions. This ability to distribute fluid to certain areas is beneficial in controlling stains made by the absorption of body fluid, such as blood or menses. By keeping the stain away from the side edges, especially in a sanitary napkin, one can give the user a sense of security that side leakage is not occurring. The separation layer 150 can be the same size and/or shape as the first material 144 but preferably will be slightly larger. The separation layer 150 can be bonded directly to the bicomponent cover 138 by adhesive, ultrasonics or by heat and/or pressure. The bonding itself is not necessary for the functionality of the separation layer 150. It should be noted that, if the bicomponent cover 138 is bonded directly to the separation layer 150, it may not be necessary to bond the first material to the second material.

Referring to FIGS. 16 and 17, still another embodiment of a bicomponent cover is shown. The bicomponent cover 152 includes a first material 154 and a second material 158. The first material 154 can be a net material, a thermoplastic film or an extrusion-coated nonwoven which has a plurality of apertures 156 formed therethrough. The second material 158, such as a nonwoven web, contains a plurality of similarly sized apertures 160 formed therethrough which are located in a central region 162. The first material 154 is bonded about its outer periphery to the lower surface of the second material 158, below the central region 162, to form a seal line 164. To facilitate manufacture, the first material 154 extends the entire length of the bicomponent cover 152, but the central region 162, which has a racetrack-shaped configuration, has a length which is only about 75% of the overall length of the bicomponent cover 152. In addition, the central region 162 is spaced apart from each of the ends of the bicomponent cover 152.

Referring to FIGS. 18 and 19, another embodiment of a bicomponent cover 166 is shown. The bicomponent cover 166 includes a first material 168 and a second material 172. The first material has a rectangular shape with a plurality of apertures 170 formed therethrough. The second material 172, such as a nonwoven web, contains a plurality of different sized apertures 174 formed therethrough which lie within a central region 176. The first material 168 is bonded about its outer periphery at 178 to the lower surface of the second material 172 and is aligned below the central region 176.

Figure 22:
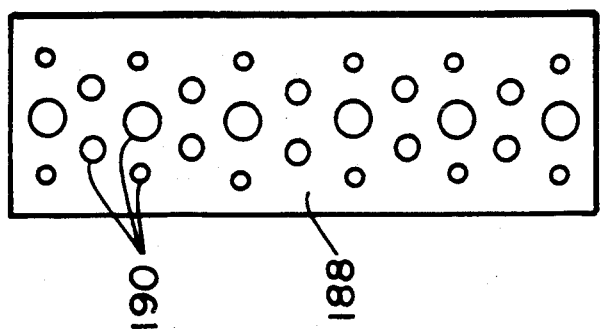
FIG. 22 is a top view of an apertured first material wherein various sized apertures are randomly arranged, and the apertures occupy at least 70% of the exposed surface area of the first material.
Figure 21:
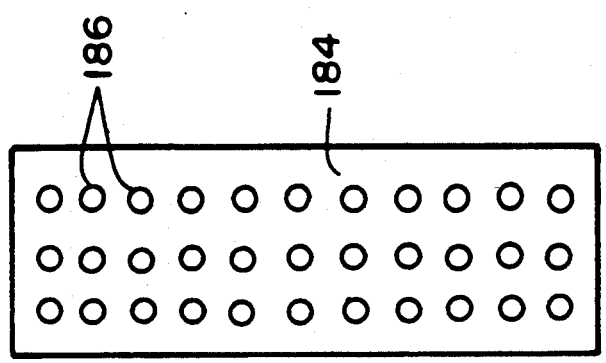
FIG. 21 is a top view of an apertured first material wherein similarly sized apertures are systematically arranged, and the apertures occupy at least 50% of the exposed surface area of the first material.
Figure 20:
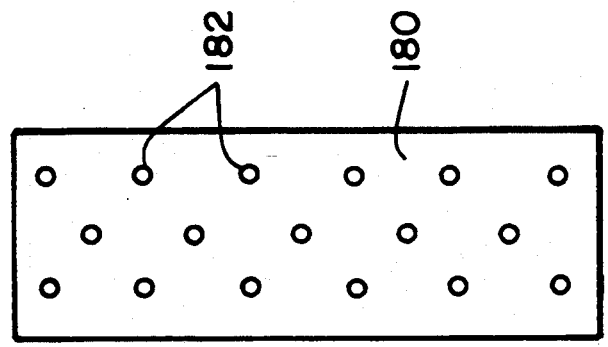
FIG. 20 is a top view of an apertured first material wherein similarly sized apertures are randomly arranged, and the apertures occupy at least 10% of the exposed surface area of the first material.

Lastly, referring to FIGS. 20-22, three strips of a first material are shown having different aperture arrangements. In FIG. 20, a strip 180 is shown having a plurality of similarly sized apertures 182 which are randomly arranged. In FIG. 21, a strip 184 is shown having a plurality of similarly sized apertures 186 which are arranged in a systematic or uniform pattern. And in FIG. 22, a strip 188 is shown having a plurality of different sized apertures 190 which are arranged to provide a large, open area relative to the total exposed surface area of the first material.

While the invention has been described in conjunction with several specific embodiments, it is to be understood that many alternatives, modifications and variations will be apparent to those skilled in the art in light of the aforegoing description. Accordingly, this invention is intended to embrace all such alternatives, modifications and variations which fall within the spirit and scope of the appended claims.

We claim:

1. A bodyside cover for an absorbent article comprising:
   a) a nonwoven web having a central region with an enlarged aperture formed therethrough, said enlarged aperture having an outer periphery; and
   b) a film material containing a plurality of apertures formed therethrough, said film material being secured to said outer periphery of said enlarged aperture and aligned below said central region, the area of said apertures formed in said film material constituting about 20-70 percent of the total exposed surface area of said film material, said film material having an absorbency rate at least equal to said nonwoven web.

2. The bodyside cover of claim 1 whereby securing said film material to said nonwoven web a stepped configuration is formed therebetween.

3. The bodyside cover of claim 1 wherein said plurality of apertures formed in said film material are of various sizes.

4. A bodyside cover for an absorbent article comprising:
   a) a first material containing a plurality of apertures constituting about 20-70 percent of the total exposed surface area of said first material, said first material being positioned about at least a portion of the longitudinal central axis of said absorbent article and constituting a primary fluid-receiving region of said cover; and
   b) a non-perforated second material having a central region with an enlarged opening formed therethrough, said enlarged opening having an outer periphery, said first material being secured to said outer periphery of said enlarged opening, said second material constituting a secondary fluid-receiving region of said cover, said second material having an absorbency rate less than said first material.

5. The bodyside cover of claim 1 wherein said apertures formed in said first material constitute about 30-60 percent of the total exposed surface area of said first material, and said first material has a rewet value which is lower than the rewet value of said second material.

6. The bodyside cover of claim 4 wherein said apertures formed in said first material are systematically arranged.

7. The bodyside cover of claim 4 wherein said second material is a nonwoven web having a rewet value of less than about 3.0 grams at 1 psi.

8. The bodyside cover of claim 4 wherein said first material has a length of at least about 50% of the length of said absorbant article and a width of between about 25-95% of the width of said absorbent article.

9. The bodyside cover of claim 4 wherein said first material has a rewet value of less than about 1.5 grams at 1 psi.

10. The bodyside cover of claim 4 wherein said first material has a length of greater than about 2 inches and a width of about 5.0 inches or less.

11. The bodyside cover of claim 10 wherein said first material has a length greater than about 2.5 inches and width of about 1.5 inches or less.

* * * * *